United States Patent [19]

Huang

[11] Patent Number: 5,265,299
[45] Date of Patent: Nov. 30, 1993

[54] STRUCTURE FOR AN ELECTRO-MOTIVE TOOTH BRUSH

[76] Inventor: Feng C. Huang, No. 31, Ta Nuan Rd., Tu Chung Hsiang, Taipei Hsien, Taiwan

[21] Appl. No.: 730,091

[22] Filed: Jul. 15, 1991

[51] Int. Cl.[5] .............................. A61C 17/34
[52] U.S. Cl. .................................... 15/22.1
[58] Field of Search ............... 15/22.1, 22.2, 22.4

[56] References Cited

U.S. PATENT DOCUMENTS 3,685,080 8/1972 Hubner ........................ 15/22.1

FOREIGN PATENT DOCUMENTS 2350898 4/1974 Fed. Rep. of Germany ....... 15/22.1

115132 8/1968 Norway ........................ 15/22.1

*Primary Examiner*—Edward L. Roberts
*Attorney, Agent, or Firm*—Yusu International Patent and Trademark Office

[57] ABSTRACT

An improved structure for an electro-motive tooth brush, which comprises a handle-shaking assembly, a connecting assembly, a water-supply assembly, and a tooth-brush assembly; the handle portion in the tooth-brush assembly is mounted to a valve of the water-supply assembly; the valve is fixedly attached to a ratchet rack of the connecting assembly; the ratchet base and the handle-shaking assembly are connected together. An eccentric wheel in the handle-shaking assembly can generate a shaking effect to cause the brush bristle portion to shake.

2 Claims, 6 Drawing Sheets

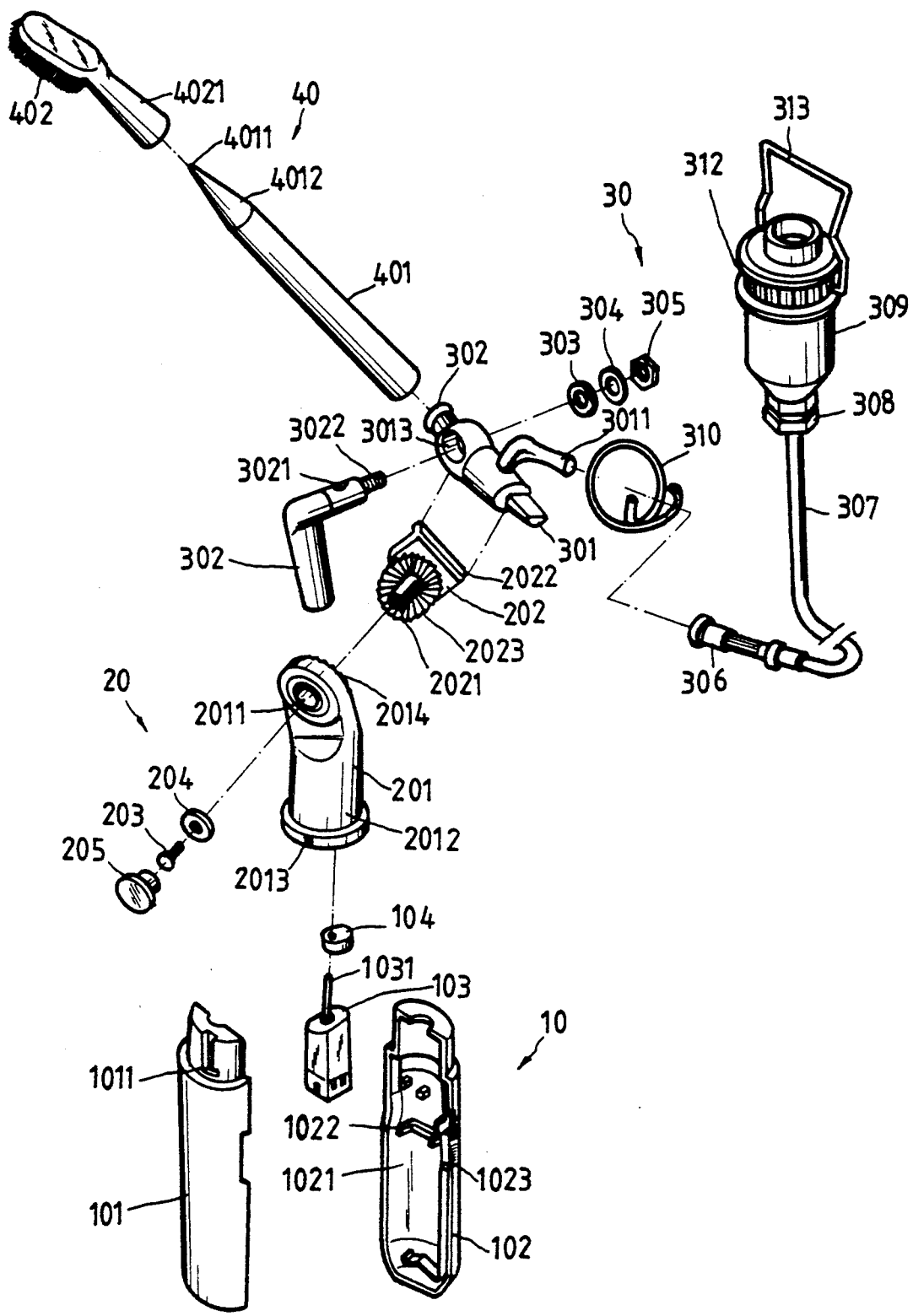
F I G. 1

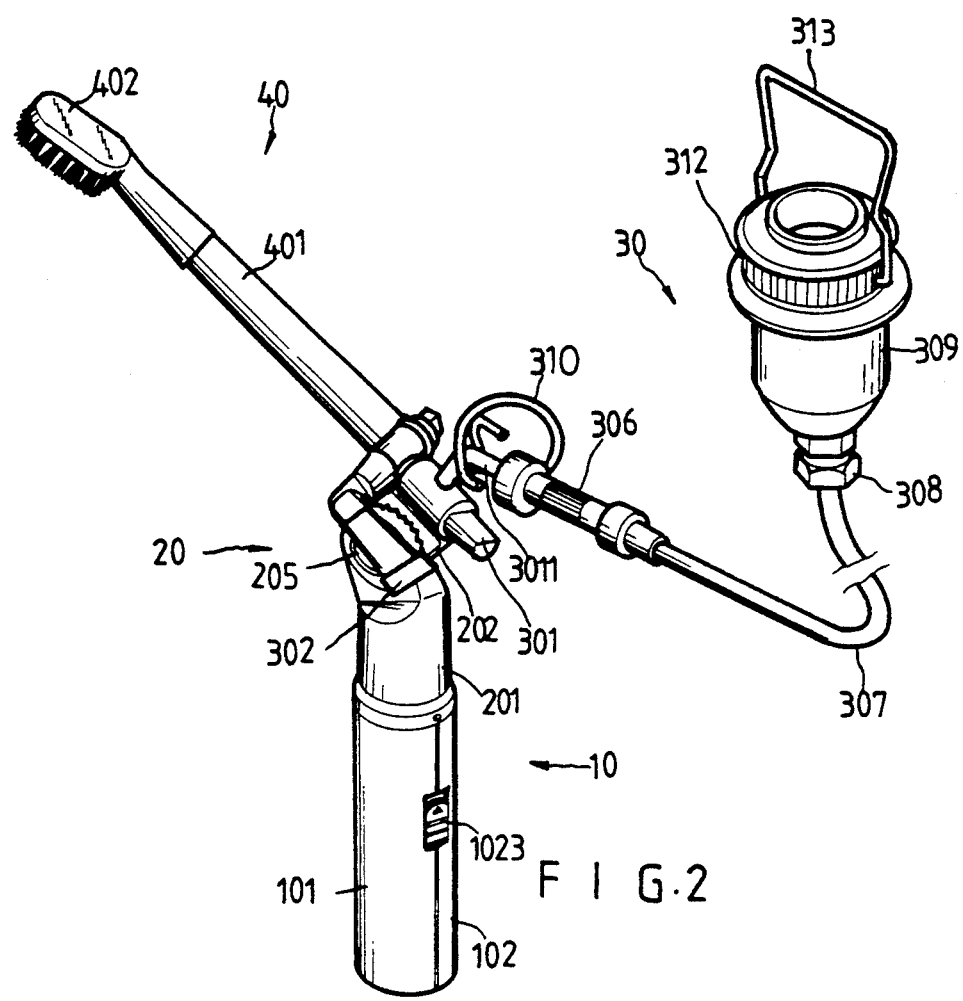
FIG. 2
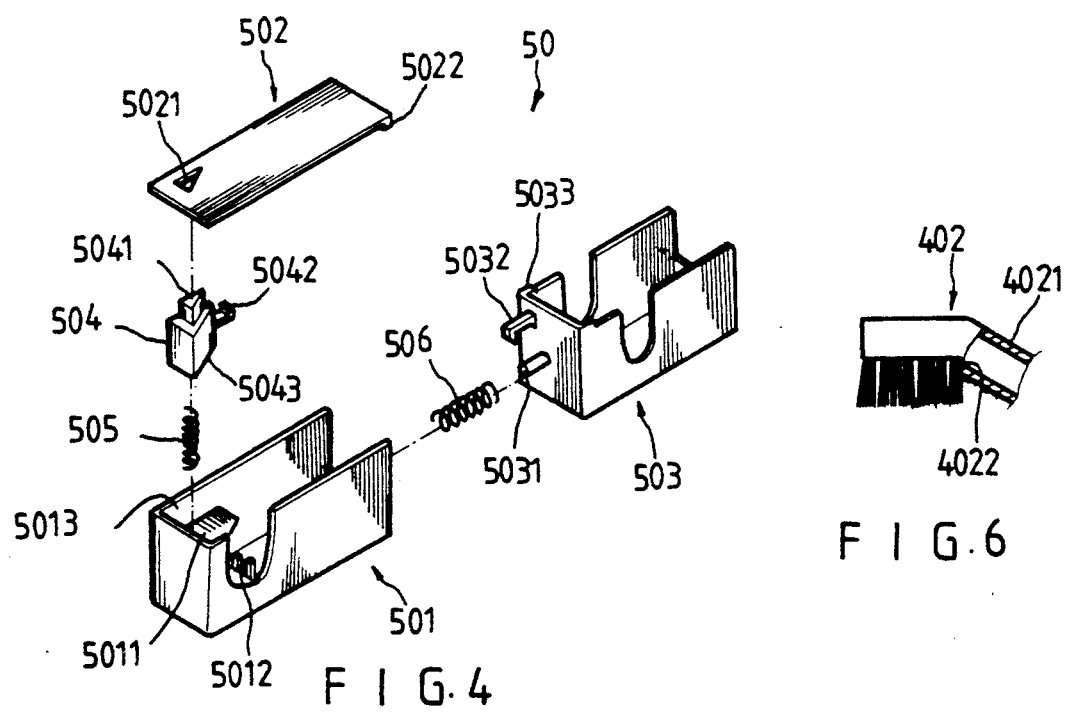
FIG. 4
FIG. 6

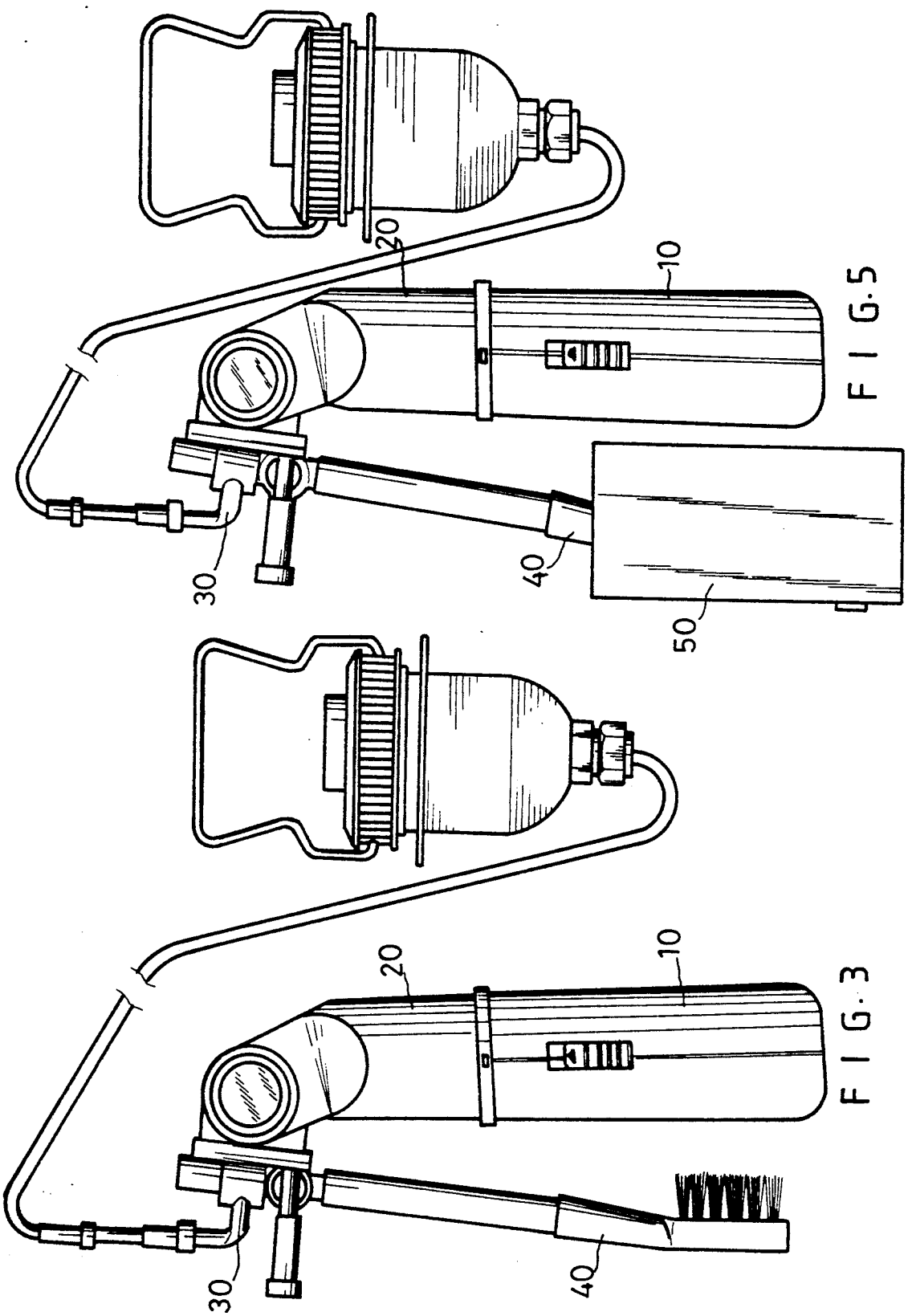

STRUCTURE FOR AN ELECTRO-MOTIVE TOOTH BRUSH

BACKGROUND OF THE INVENTION

A conventional tooth brush usually comprises a brush bristle portion and a handle portion. A user can hold the handle portion to brush his or her teeth by moving the brush back and forth. After the brushing movement, a user has to drink or gargle water from a glass or cup to wash his/her mouth; in other words, the glass or the like becomes an indispensable item with the tooth brush. Carrying such a glass just for brushing teeth in the event of leaving home or traveling is rather inconvenient.

SUMMARY OF THE INVENTION

This invention relates to an improved electro-motive tooth brush, which comprises a brush handle assembly, a handle-shaking assembly, and a water-supply assembly. The brush handle assembly is connected with the water-supply assembly by means of a water valve that permits water to flow through the handle to the brush for rinsing the person's mouth. A motor in the handle-shaking assembly drives an eccentric weight to generate a shaking effect, thereby causing the brush bristle portion to shake and exert a massage action on the person's teeth.

The prime feature of the present invention is to provide an improved electro-motive tooth brush, wherein the handle-shaking assembly causes the tooth brush to rub along the tooth surfaces, thereby improving the tooth brushing operation and at the same time providing a massage effect to the teeth.

Another feature of the present invention is an improved electro-motive tooth brush, in which a faucet-attachment sleeve and water hose are used for connecting the tooth brush to a water supply, whereby a suitable water volume can flow through the brush bristles for rinsing the person's mouth and removing any remaining tooth paste or other particles.

Still another feature of the present invention is an electro-motive tooth brush that is foldable for compact storage.

BRIEF DESCRIPTION OF THE DRAWINGS

FIG. 1 is a perspective view of one embodiment according to the present invention taken with the component-parts in a disassembled condition.

FIG. 2 is a perspective view taken in the same direction as FIG. 1, but with the parts assembled.

FIG. 3 is a side elevational view of the FIG. 2 toothbrush assembly.

FIG. 4 is a disassembled view of a cap member usable with the FIG. 3 toothbrush assembly.

FIG. 5 is a view taken in the same direction as FIG. 3, but with the FIG. 4 cap member installed on the bristle assembly.

FIG. 6 is a sectional view of the brush bristles according to the present invention.

DETAILED DESCRIPTION

Figure 7:
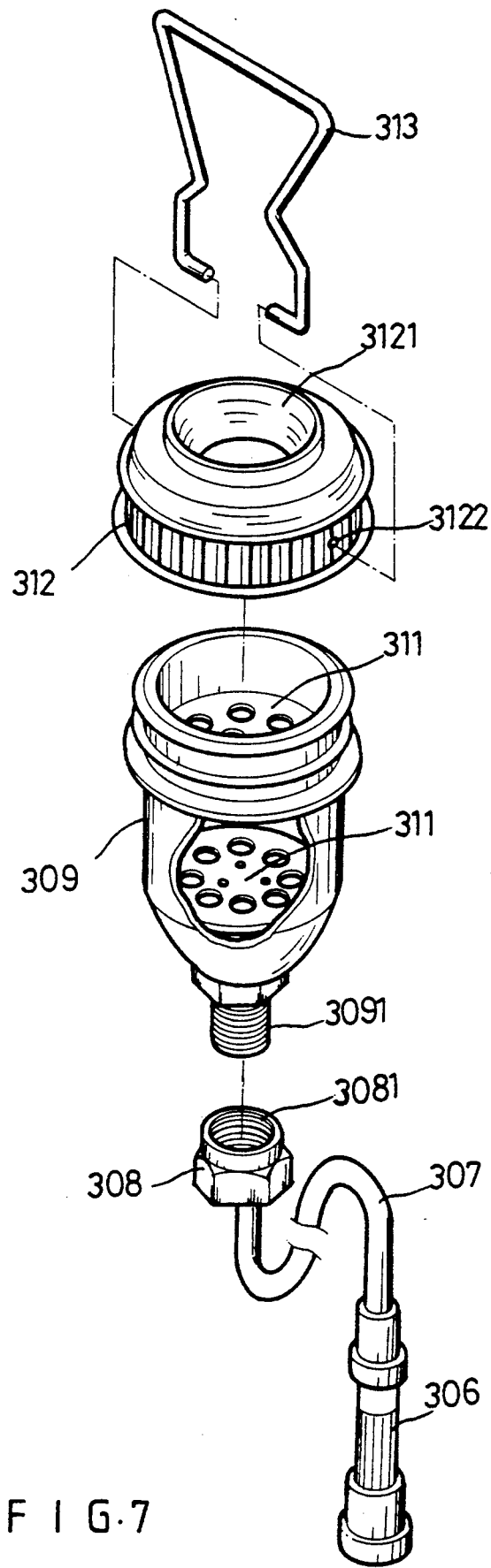
FIG. 7 is a disassembled view of a water supply assembly according to the present invention.

FIGS. 1 and 2 illustrate a disassembled view and a perspective view of one embodiment of the present invention, which comprises a handle shaking assembly 10, a connecting assembly 20, a water-supply assembly 30, and a brush assembly 40. The handle shaking assembly 10 includes two opposed semi-cylindrical housing portions 101 and 102 mated to each other. The housing portion 102 includes a battery chamber 1021, a motor base 1022 for a motor 103, and a control switch 1023. The other housing portion 101 is a hollow member having a bayonet groove 1011; the housing body portion 102 has a similar bayonet groove (not shown). A motor 103 is mounted on a motor base 1022 so that the motor shaft 1031 extends out of the housing body portions 101 and 102 to mount an eccentric weight 104.

The connecting assembly 20 includes a hollow base 201 having ratchet teeth 2014 engageable with ratchet 2023 on a plate 202. The lower part of the hollow base 201 is formed into a hollow cylindrical member 2012, the inner wall surface of which has a fastening lugs 2013 matable with the aforementioned bayonet grooves 1011 on members 101 and 102 when member 2012 is telescoped onto members 101 and 102. A round hole 2011 in base 202 accommodates an internally threaded boss 2021, such that a pivot screw 203 can be extended through a pad 204 and round hole 2011 into the threaded boss 2021 to hold plate 202 in selected positions of pivotal adjustment on member 201. A cap 205 is attached to the screw 203 for decorative purposes.

The water supply assembly 30 includes a valve body 301, which has a water intake tube 3011 on one side thereof, and a water outlet opening 3012 in one end thereof. Both the water intake tube 3011 and the water outlet opening 3012 are in communication with each other via an internal passage in valve body 301. Valve body 301 has a transverse round bore 3013, in which an L-shaped plug rotary valve and handle 302 is pivotally mounted. The rotary plug valve and handle unit 302 is held in bore 3013 by means of packing rings 303 and 304, and a nut 305 is held in bore 3013 by means of packing rings 303 and 304, and a nut 305 threaded on the threaded portion 3022 of the handle-plug valve unit. The rotary unit 302 has a through round hole 3021, which can be aligned with the valve body passage or oriented perpendicular to the passage so as to control the water flow through the water outlet opening 3012.

Figure 8:
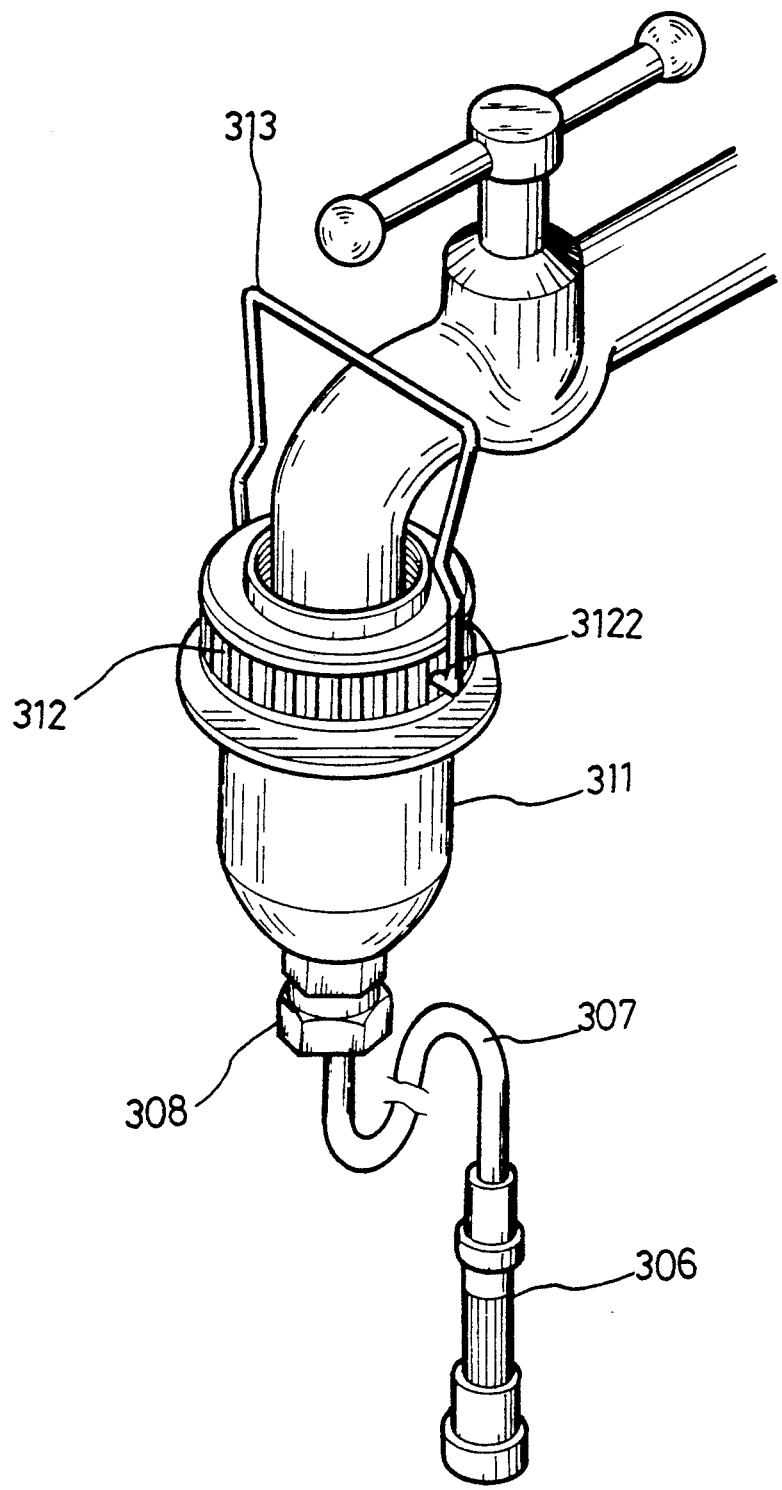
FIG. 8 illustrates the FIG. 7 water supply assembly connected with a water faucet.
Figure 9:
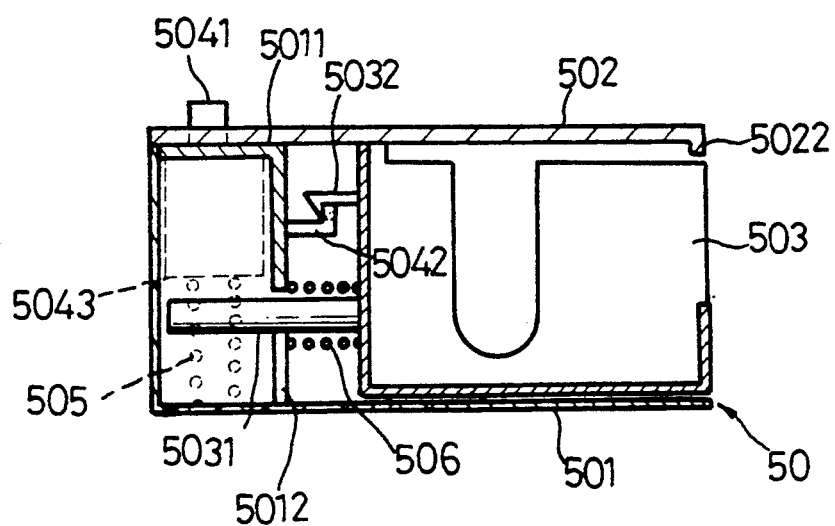
FIG. 9 is a sectional view taken through the cap structure shown in FIG. 4.

Referring to FIGS. 7 and 8, the water intake tube 3011 may be connected with a joint 306 and one end of a hose 307. The other end of hose 307 is joined to a sleeve 309 by a joint 308 that include inner threads 3081 and outer threads 3091. The sleeve 309 is a hollow cylinder with a through hole (not shown) at the lower end thereof; in the sleeve 309, there are two water retarding disks 311 for reducing the impact force of water. A cap 312 is mounted on the sleeve 307. As shown in FIG. 7, the cap has a round hole 3121, through which clean water can flow. Side areas of the cap 312 are furnished with two holes 3122, in which a hook ring 313 is attached pivotally whereby the sleeve 309 can be hung on a faucet (as shown in FIG. 8). The round hole 3121 of the cap 312 connects with the faucet to let water flow into the sleeve 309 and through the water retarding disks 311 into hose 307.

The brush assembly 40 includes a tubular handle portion 401, and brush bristle portion 402. The handle portion 401 is a cylindrical member with a through hole 4011 therein acting as a flow passage; the front end of the handle portion 401 is formed into a conic configuration 4012. The brush bristle portion 402 (as shown in FIG. 6) has one end formed into a round pipe portion 4021 with an opening 4022; the round pipe portion 4021 is to be attached to the conic portion 4012 of the handle portion 401.

After the handle-shaking portions 101 and 102 are assembled together, the bayonet grooves 1011 in portions 101 and 102 will be engaged with the fastening lugs 2013 on the lower end of the ratchet base 201 so as to attach the handle-shaking assembly 10 to the connecting assembly 20. The aforementioned valve body 301 is fixedly attached (such as by using a glue) to surface 2022 of the ratchet plate 202 of the connecting assembly 20. The toothbrush assembly 40 is connected to the valve body 301 of the water-supply assembly 30 to form the assembly shown in FIG. 2.

To operate the tooth brush, a user turns on the switch 1023 so that battery current is applied to the motor 103, which rotatably drives the eccentric weight 104 so as to cause the brush bristle portion 402 on the tooth-brush assembly to produce a shaking and massaging effect during the tooth brushing operation. The sleeve 309 of the water-supply assembly 30 is connected with a water faucet to let water flow into the valve body 301 through the hose 307. By turning the rotary handle 302 the user can let a suitable water volume flow through the handle portion 401 to the opening 4022 of the brush bristle portion 402 so as to provide the user with water to wash his or her mouth. When not in use, the FIG. 2 assembly can be folded around the central axis defined by screw 203 and the ratchet teeth 2014 and 2023 so as to shorten the assembly for convenient storage. (as shown in FIG. 3).

FIG. 4 illustrates a disassembled view of a cap member 50 according to the present invention. The cap member includes a box 501, an upper cover 502, an inner box 503, a push button 504 and two springs 505 and 506. The box 501 is a rectangular box open on its top and one side. A block member 5011 therein has a groove 5012 for receiving pin 503 that extends from inner box 503 through a spring 506. A rectangular channel 5013 is provided beside the block member 5011 to accommodate push button 504. One end of the inner box 503 has a fastening hook 5032, and a positioning flange 5033. The upper cover 502 is a rectangular plate element having a triangle hole 5021 at one end thereof and a depending flange 5022 at the other end thereof. The push button 504 has a triangle stud 5041 projecting upwardly from a rectangular stud 5043; a fastening hook 5042 extends from stud 5043 for connection with the aforementioned hook 5032. When the inner box 503 tends to slide outwards as a result of the pushing force of spring 506, the stud 5041 on the push button 504 extends out of the triangular hole 5021 in the upper cover 502 because of the action of spring 505 that is positioned under the rectangular stud 5043 of the push button 504; upper cover 502 is fastened on the box 501 to form a complete cap member 50. The inner box 503 in the box 501 is normally slid outwards as a result of the spring 506, but the inner box 503 is unable to completely separate from box 501 because the positioning flange 5033 is retained by the cover flange 5022.

In use of the FIG. 4 cap member, bristle portion 402 of the tooth-brush assembly 40 is put in the inner box 503, and the inner box 503 is then pushed into the box 501 all the way until the fastening hook 5032 of the inner box 503 is engaged with the fastening hook 5042 of the push button 50. The brush bristle portion 402 can thus be stored in the cap member 50 for protection (as shown in FIG. 5). The brush bristle portion 402 can be pulled out by pressing the triangle stud 5041 of the push button 504, such that push button 504 is pressed downward to have the fastening hook 5042 disengaged from the fastening hook 5032 on the inner box 503; the inner box 503 will automatically slide out as a result of the force of spring 506.

I claim:

1. A toothbrush comprising an elongated tubular handle (401); a brush bristle means (402) connected to one end of said tubular handle; a manual water valve means connected to the other end of said handle for delivering water through the handle to the bristle means; said valve means comprising a valve body (301) having a transverase bore (3013) and an adjustable valve element (302) extending within said transverse bore for alternately stopping or permitting water to flow through the valve body into the tubular handle; means for supplying water to said valve means; said water supply means comprising a sleeve (309) insertable on the end of a water faucet, and a flexible hose extending from said sleeve to said valve means so that when the faucet is in an open condition water is enabled to flow through the hose to the valve means; and means for imparting a vibrating force to said tubular handle whereby the brush bristle means exerts a massage action on the user's teeth; said vibrating force means comprising a motor housing (101,102), an electric motor (103) within said housing, an eccentric weight (104) mounted on the motor drive shaft, and an adjustable connection comprising two pivotably related connector elements attached, respectively, to the valve body and motor housing, whereby said motor housing can be folded into a storage position extending alongside the tubular handle or unfolded to an operating position extending at a substantially angle relative to the tubular handle.

2. The toothbrush of claim 1, wherein said adjustable connection comprises a pivot pin extending through said connector elements to define a pivot axis; said connector elements having opposed facing ratchet teeth radiating from said pivot axis, whereby said connector elements can be maintained in selected positions of pivotal adjustment.

* * * * *